United States Patent [19]

Itil et al.

[11] Patent Number: 5,273,037
[45] Date of Patent: Dec. 28, 1993

[54] ELECTRODE ASSEMBLY FOR EEG HEADSET

[76] Inventors: Turan M. Itil, 150 White Plains Rd., Tarrytown, N.Y. 10591; Emin Eralp, 11 Eastern Ave., Ossining, N.Y. 10562

[21] Appl. No.: 739,253

[22] Filed: Aug. 1, 1991

[51] Int. Cl.⁵ .............................................. A61B 5/04
[52] U.S. Cl. .................................... 128/644; 128/731
[58] Field of Search .................. 128/644, 639, 731, 791

[56] References Cited

U.S. PATENT DOCUMENTS

| | | | |
|---|---|---|---|
| 2,208,023 | 8/1937 | Ellis | 128/639 |
| 2,409,033 | 10/1946 | Garcean | 128/644 |
| 4,632,122 | 12/1986 | Johansson et al. | 128/644 |
| 4,683,892 | 8/1987 | Johansson et al. | 128/639 |
| 4,800,888 | 1/1989 | Itil et al. | 128/644 |

OTHER PUBLICATIONS

"A Method for Locating Scalp Electrodes in Spherical Coordinates" Ary et al., IEEE Publications 1981, p. 836.

*Primary Examiner*—Lee S. Cohen
*Assistant Examiner*—Jeffrey R. Jastrzab
*Attorney, Agent, or Firm*—Evelyn M. Sommer

[57] ABSTRACT

An electrode assembly for an EEG headset has a cylinder and piston, at least one disk-shaped mounting element with an inner portion for mounting the cylinder therethrough and an outer portion overlapping onto the liner of the headset, an electrode body made of insulative material mounted to the piston and holding an electrode tip, and an electrode tip made of conductive material with a wire lead for transmitting electrical signals from the tip to an external signal processing unit separately from the rest of the electrode assembly. Preferably, the mounting element is a pair of rubber washers supporting the cylinder from each side of the liner. The electrode body has a threaded end for threading in the piston, and a central passage for supplying electrolyte gel to the electrode tip. The electrode tip has a disk shape with a relatively large surface area for maintaining good contact with the subject's scalp. The electrode body may also have a ball joint between its piston-mounting portion and tip-holding portion other types of electrode tips may be mounted on the assemblies. The headset and electrode structures provide a shorter signal transmission system, which greatly reduces extraneous noise, and allow for direct connection to an external recording or EEG device. The headset may include signal conditioning hardware in the form of a VLSI digital amplifier/signal conditioning unit that can output analog, digital, or telephonic modulated EEG signals, or an FM telemetry system mounted on the headset for wireless transmission.

13 Claims, 4 Drawing Sheets

ELECTRODE ASSEMBLY FOR EEG HEADSET

FIELD OF THE INVENTION

This invention generally relates to an electrode assembly for a headset for electroencephalographic (EEG) testing, and more particularly, to an improvement in the electrode assembly which reduces the instrument's susceptability to erroneous or spurious signals and improves the recordation of brain activity signals.

BACKGROUND ART

An EEG instrument is a clinical, multichannel device used to measure and display the brain waves of a subject. The subject's brain waves are monitored by the use of a number of electrodes placed in contact with the scalp in a predetermined pattern or montage (typically, of nineteen locations) which is well known in the art. The electrical activity generated by the subject's brain, i.e., brain waves, are detected as electrical signals by these electrodes and transmitted to a signal monitoring unit where they are amplified and processed into graphic representation for viewing and diagnostic interpretation.

For many years the state of the art of electrode design and placement was rather primitive in relation to advances in the processing and analysis of EEG signals. Location and placement of the electrodes on the subject's scalp was done by trial and error techniques which were cumbersome, time-consuming, and unreliable. The state of the art was advanced by the development of a headset for EEG tests having the electrodes mounted in their proper positions and actuatable in good electrical contact with the scalp, for example, as disclosed in U.S. Pat. Nos. 4,632,122 and 4,683,892 issued to N. Johansson, E. Eralp, and T. Itil, and U.S. Pat. No. 4,800,888 issued to T. Itil, D. Shapiro, E. Eralp, and N. Johansson, which are incorporated herein by reference.

As illustrated in FIGS. 1 and 2 herein, the EEG headset 10 of Johansson, Eralp, and Itil includes a helmet liner 12 with a plurality of electrodes 20 placed at predetermined positions about the liner 12. In order to accommodate each of the electrodes 20, apertures 22 are provided in the liner 12 and a resilient mesh 24 is used to hold the respective electrodes in position within the apertures 22. The mesh 24 permits ventilation of air through the liner 12, thus making the headset 10 more comfortable to wear, and its resilience allows the technician to oscillate the electrode tips to displace the subject's hair for placement in contact with the scalp. The electrodes 20 have respective tips 50 with ends that are to be placed in electrical contact with the scalp. Individual air-actuated cylinder and piston arrangements displace the respective electrode tips 50 against the scalp when air pressure is supplied through air conduits 70 fed by feed line 110 from an air pump 100. Conduits 53 are used to supply an electrolyte fluid or gel to the electrode tips 50 to ensure good electrical contact with the scalp. The electrolyte is supplied to the conduits 53 from a feed line 120 connected to an external electrolyte supply.

The EEG headset and air-actuated, electrolyte-supplied electrode assembly of Johansson, Eralp, and Itil provide a significant advance in the art of EEG instruments. However, it has been observed that the electrodes of the EEG headset, and of EEG instruments generally, are susceptible to sporadic signal spikes, high voltage artifacts, rhythmical slowing in the Theta wave range, and polarization. In addition, the headset and electrode assemblies require certain improvements to maintain them more stably yet flexibly on the subject's head.

SUMMARY OF THE INVENTION

In accordance with the invention, an electrode assembly for an EEG headset, of the type having a liner provided with apertures for mounting respective electrode assemblies therethrough, comprises an electrode cylinder including a movable piston at an interior side thereof, at least one mounting element made of a flexible material for flexibly mounting an electrode of said assembly through a respective aperture in the liner, said mounting element generally having a disk shape and being provided with an inner portion with an annular hole for mounting the electrode cylinder therethrough and an outer portion extending beyond the aperture so as to be supported overlapping on the liner, an electrode body made of an electrically insulative material having one portion for mounting to an end of the piston and another portion for holding an electrode tip, and an electrode tip made of a conductive material mounted to an end of the electrode body and having a conductive lead encapsulated in an insulative shielding connected thereto for transmitting electrical signals obtained by the electrode tip to an external signal processing unit separately from the electrode cylinder and other parts of said assembly.

In the preferred embodiments, a pair of mounting elements in parallel are mounted to the electrode cylinder and support it from each side of the liner. The mounting element is a rubber washer with an inner ring which fits onto the electrode cylinder and an outer ring for mounting onto the liner which is connected to the inner ring by radial spokes. The electrode body has a threaded end for threading into a correspondingly threaded receptacle end of the piston to allow convenient replacement. The electrode body also has a central passage communicating with an inlet connected to a conduit for supplying an electrolyte fluid or gel to the electrode tip. The electrode tip is preferably a standard electrode disk having a relatively large surface area, e.g., a 10 mm. diameter cup-shaped disk with a 2 mm. center hole for passage of the electrolyte. Another embodiment employs a ball joint between the piston-mounting portion and the tip-holding portion. The leads from the electrode tips are passed through openings between the radial spokes in the mounting elements and the apertures in the liner for connection to the external signal processing unit.

Other objects, features, and advantages of the present invention will become apparent from the following detailed description of the best mode of practicing the invention when considered in conjunction with the drawings, as follows:

DESCRIPTION OF THE PREFERRED EMBODIMENTS

Figure 1:
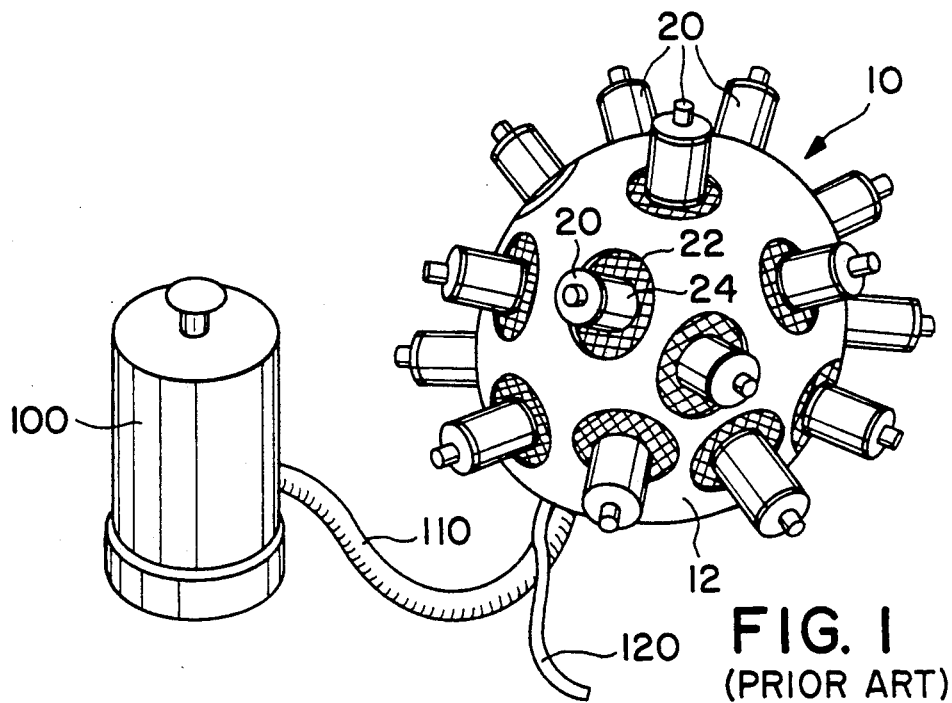
FIG. 1 is a perspective external view of a headset for EEG testing of the prior art.
Figure 2:
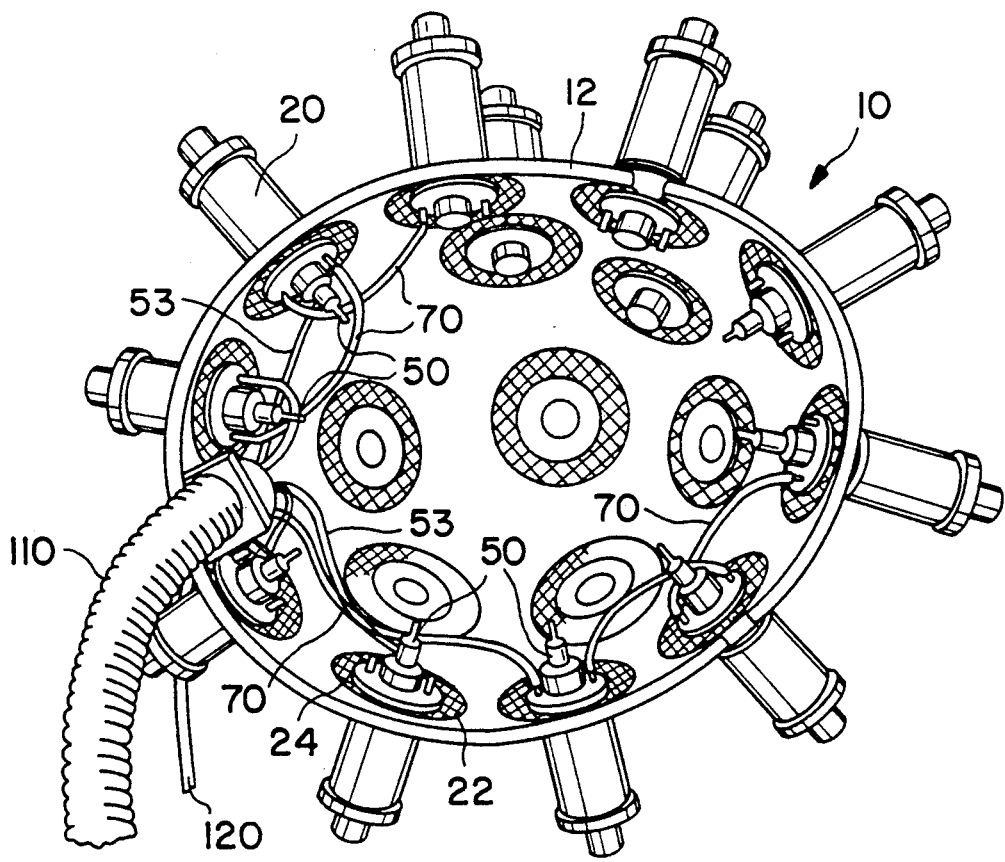
FIG. 2 is a perspective internal view of the EEG headset of FIG. 1.
Figure 3:
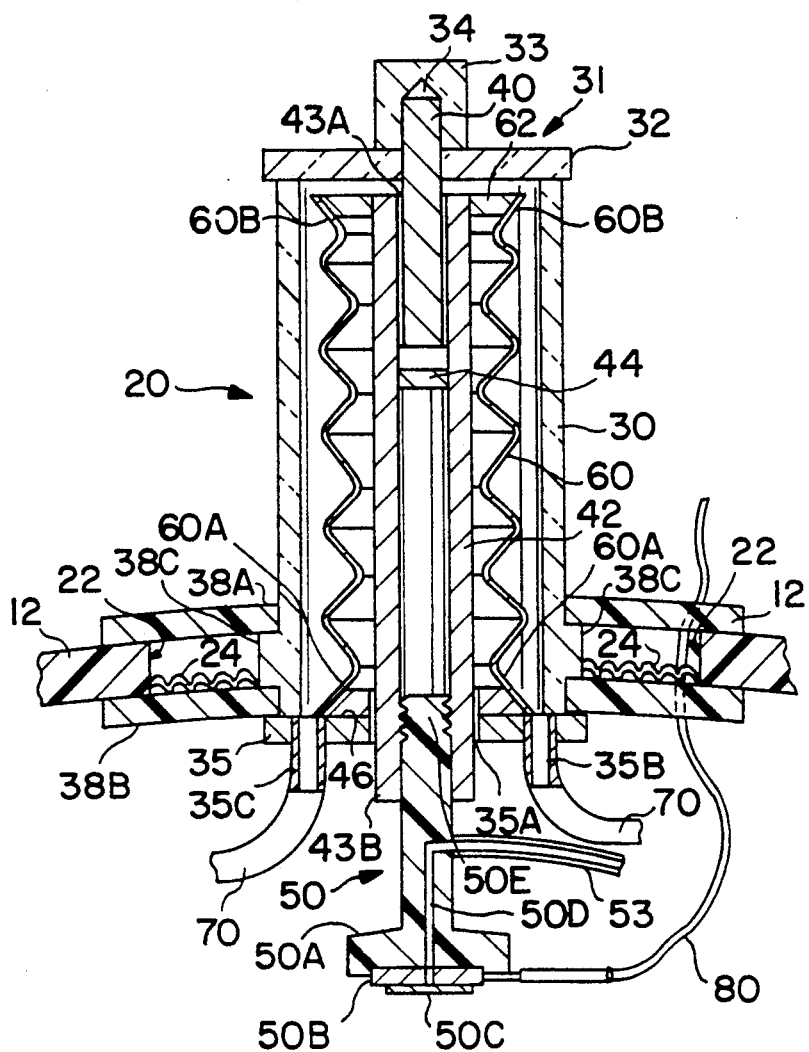
FIG. 3 is a sectional view of one embodiment of an improved electrode assembly to be used in an EEG headset in accordance with the invention.
Figure 4:
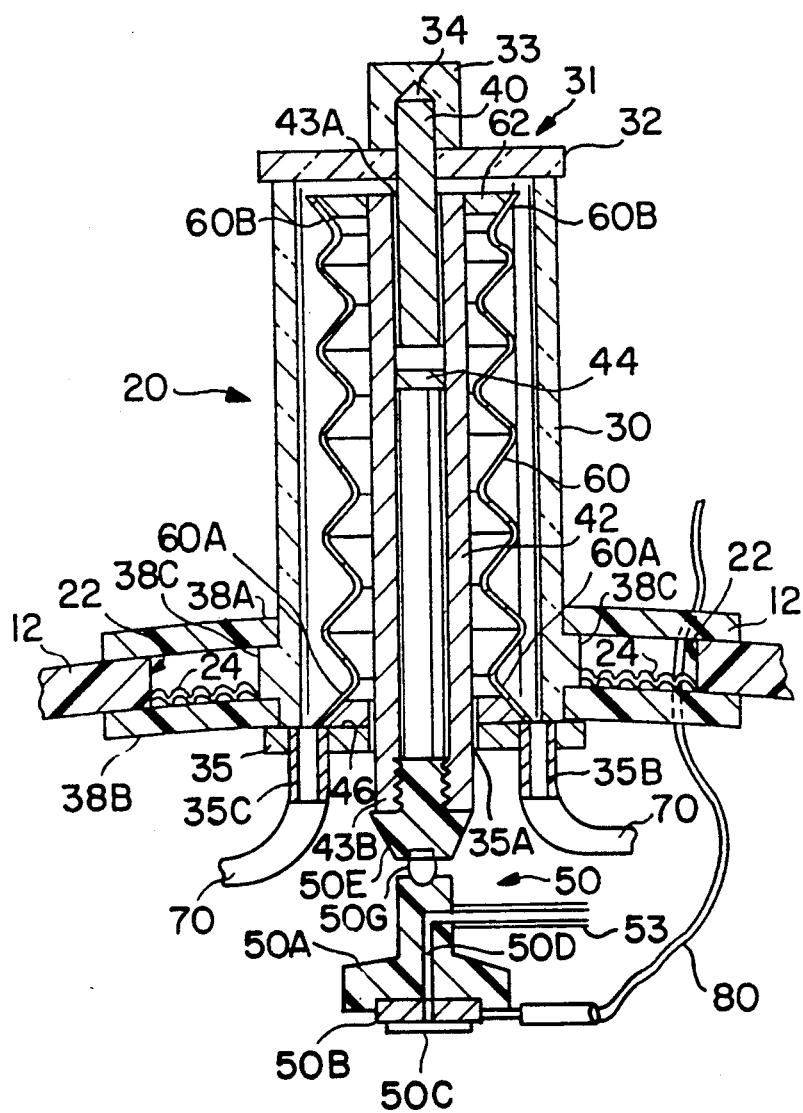
FIG. 4 is a sectional view of another embodiment of an improved electrode assembly to be used in an EEG headset in accordance with the invention.

FIGS. 3 and 4 show two embodiments of an improved electrode assembly for an EEG headset. Each electrode 20 is mounted through a respective aperture 22 in a liner 12 of the EEG headset. The electrode assembly includes an outer cylinder 30 captured in a resilient mesh 24 which is adhesively bonded about the outer periphery of the cylinder 30 below a circular lip 38C. The cylinder 30 is sealed at its upper end 31 by an end cap 32 and a top cap 33. A center aperture 34 is provided through both the end cap 32 and the top cap 33. A post 40 is bonded to both the end cap 32 and top cap 33 and extends downwardly into the interior of the cylinder 30.

A hollow piston rod 42 having an upper end 43A and a lower end 43B and a center plug 44 is provided within the cylinder 30. The back end 43A of the piston rod is slidably mounted on the post 40. Piston rod 42 is bonded about its outer periphery to a bottom cap 35 which includes a center aperture 35A through which the piston rod 42 passes, as well as an air inlet 35B and an air outlet 35C connected to air conduits 70. A bellows 60 is sealed at the forward end to a shoulder 46 on the bottom cap 35 at points 60A, and at the back end to a flange 62 on the back end of the piston at points 60B. The piston rod 42 is actuated to move toward the scalp of the subject by air pressure supplied through inlet 35B which creates an expansion pressure against the flange 62 and compresses the bellows 60. For retraction, the air pressure is released through air outlet 35C.

Further details of the structure and operation of the underlying components of the electrode assembly for the EEG headset are provided in the disclosures of U.S. Pat. Nos. 4,632,122 and 4,683,892 of Johansson, Eralp, and itil, which are incorporated herein by reference. The following description is directed more specifically to the improvements to the electrode assembly provided in accordance within the present invention.

Figure 5:
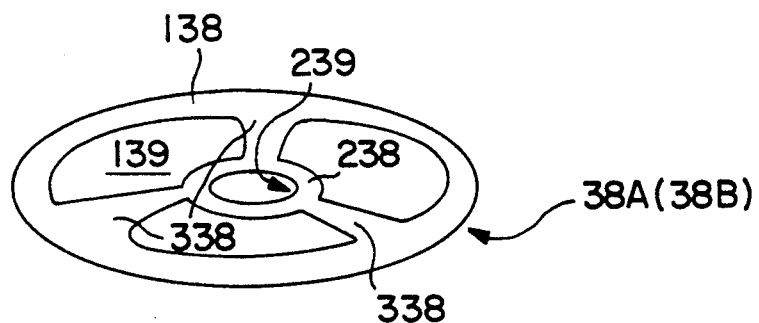
FIG. 5 is a perspective il n of a rubber washer mounting element for the electrode as assembly.

Referring to FIG. 3, a first embodiment of the electrode assembly has a pair of mounting elements 38A and 38B made of a flexible material for flexibly mounting the electrode 50 through the aperture in the liner. As shown more clearly in FIG. 5, the mounting element 38A, 38B has a disk shape with an inner portion 238 with an annular hole 239 for mounting the electrode cylinder therethrough and an outer portion 138 which is dimensioned to extending beyond the aperture so as to be supported overlapping on the liner. Preferably, the mounting element is a rubber washer with spokes 338 connecting the inner ring 238 and the outer ring 138. Openings 139 are provided between the spokes 338. The inner rings 238 of the rubber washers 38A, 38B are elastically fitted onto the cylinder 30 abutting above and below the lip 38C, while the outer rings 138 extend over the liner 12. A bead and groove arrangement may be formed on respective parts of the outer ring 138 and the supporting edge of the liner 12 for securing the rubber washer in position.

The rubber washers hold the electrode assemblies to the liner in a stable yet flexible manner. The mesh 24 may be omitted as the washers can be formed to have sufficient rigidity and holding strength. The flexibility of the rubber washers affords a desired degree of rotational or oscillatory movement to the cylinder 30. This is useful to reduce impedances to the placement of the electrodes in contact with the scalp, e.g. by allowing obstructing hair to be parted. The rubber washers also provide flexibility in the direction perpendicular to the scalp, which allows the placement of the electrodes to conform better to the contours of the subject's head. The use and spacing apart of the two washers provides additional stability and allows differential pressure to be spread between them.

In accordance with another feature of the invention, the electrode 50 has an electrode body or base 50A made of an electrically insulative material. The base has a threaded end 50E for threading into a correspondingly threaded receptacle end of the piston rod 42 to allow convenient replacement. The electrode body 50A also has a central passage 50D communicating with an inlet connected to the conduit 53 for supplying the electrolyte fluid or gel to the electrode tip 50B. The use of the insulated electrode body 50A allows the electrode tip 50B to be electrically isolated from the rest of the electrode assembly.

The electrode tip 50B is made of conductive metal and is held to the projecting end of the electrode body 50A. The tip 50B has a wire lead 80 encapsulated in an insulative shielding connected thereto for transmitting electrical signals to an external signal processing unit. The wire lead 80 is passed through the opening 139 between the radial spokes 338 in the rubber washer mounting elements 38A, 38B.

The use of separate wire leads avoids the practice in the prior art of forming an electrical connection from the electrode tip through the contact between the metal threading of the electrode body in the piston rod end. Such threading can accumulate contaminants or other deposits which can result in noise, unreliable transmission of signals, and/or unequal conduction areas for the threads of the different electrode assemblies.

Also, the prior practice of forming the electrode body and its electrical contact through the piston out of metal made the exposed conductive parts of the assembly prone to picking up extraneous noise. The problem was compounded when different metals or different alloys were used between the connecting metal parts, because of spurious voltages caused by electrolytic effects between the different metals. In this invention, only the electrode tip need be made of metal, whereas the remainder of the electrode assembly, including the electrode base, piston, and cylinder can all be made of non-metallic material.

Also, the electrode tip is preferably a disk of relatively large area. It has been observed by the inventors that the prior practice of using a small-area pointed tip caused spiking in the electrical signal if the electrode tip was moved or was not perfectly perpendicular to the scalp or if movement of the subject's head caused contact with the small-area tip to be separated momentarily. The larger tip area is spread out over a greater area of scalp contact and ensures that noise and other spurious signals will be kept low despite movement of the electrodes and the scalp. The larger tip area also affords a greater area for contact between the electrolyte gel 50C and the scalp.

The electrode structure of the invention permits the use of conventional electrode disks such as, for example, standard gold or silver cup-shaped disks of 10 mm. diameter with a 2 mm. central hole, designated E5GH or E5SH, made by Grass Instruments, Inc. The material of these electrode disks is heavy gold plate over solid silver. The central hole of the conventional cup-shaped disks allows the electrolyte gel to be delivered to the scalp through the inner passage of the electrode body 50A. The electrode structure of the invention permits the use of completely different (non-disk type) conventional electrodes, e.g., Alvar electrodes, as well.

A modified version of the electrode body 50A is shown in FIG. 4 having a threaded plug portion 50E which threads into the piston end and a ball joint 50G connecting it to the rest of the electrode body. The ball joint 50G allows the projecting end of the electrode body 50A to swivel in order to accommodate and follow small movements of the subject's head, thereby avoiding interference with or the breaking of electrical contact between the electrode tip 50B and the subject's scalp. A further improvement of the helmet signal acquisition system includes much shorter signal transmission hardware made possible by a 25-pin (or up to 90-pin) D-connector, which is mounted on the back of the headset. All electrodes are plugged into this connector. A standard ribbon cable is used to connect the headset to any recording device. Alternatively, micro-signal conditioning hardware can be mounted directly to the 25-pin D-connector or separately to each electrode. On the other end of the ribbon cable, adapters can be plugged into a conventional headboard or directly to the EEG machine bypassing the headboard, thus greatly reducing the possibility for extraneous noise.

With the above-described construction for the EEG headset and its electrode assemblies, it is found that sporadic signal spikes, high voltage artifacts, rhythmical slowing in the Theta wave range, and polarization in the EEG signals are largely eliminated. In addition, the headset and electrodes can be maintained more stably and flexibly on the subject's head.

The preferred embodiments described herein may be modified for the inclusion of two types of signal conditioning hardware. The first signal conditioning hardware is a digital amplifier/signal conditioning unit. The unit is a VLSI integrated system for signal acquisition, amplification, conditioning, filtering, and output to a recording or analysis device.

The first modified hardware is made up of the following modular components. A data transmission cable is attached to the previously mentioned D-connector, and is intentionally kept short so that no spurious extraneous electrical noise is intercepted in the data transmission path. An input selector is provided so that any combination or all of the nineteen headset electrodes can be selected for input. Signal amplification controls are provided to amplify the signals for better signal-to-noise resolution. Signal conditioning circuitry is provided including an A/D converter, digital bandpass filter, line noise filter, and input reformatting circuitry. A data output module can be configured to provide either analog output (using a D/A converter) for conventional EEG machines or writer units, or telephone modulating circuitry enabling the system to perform as a telephonic EEG transmission unit, or digital data output directly to digital data recorders or computers for analysis. The hardware system has a user interface panel corresponding to the application it is used for, so that the appropriate electrode inputs, filter ranges, and amplification factors can be selected by the user. A CRT display may be used for display of selection parameters or the input signals for monitoring purposes. The hardware may also include a battery power supply for portability and patient safety. The hardware arrangement allows the headset system to be a complete bioelectrical signal recording system that is compact and self-contained.

The second hardware arrangement is a derivative of the above-described arrangement, and includes a microelectronic telemetry system which mounts directly on the D-connector, thus eliminating the need for any data transmission lines. The microelectronic telemetry system is made up of a preamplifier module mounted on each electrode assembly to increase the signal-to-noise ratio and coupled to a multiplexer with FM transmitter chip mounted on the D-connector. These components are thus part of the headset. Remote from the headset, an FM receiver/decoder decodes the converted bioelectrical signals and transfers digitized signals to a digital data recorder and/or a computer for further analysis.

Figure 6A:
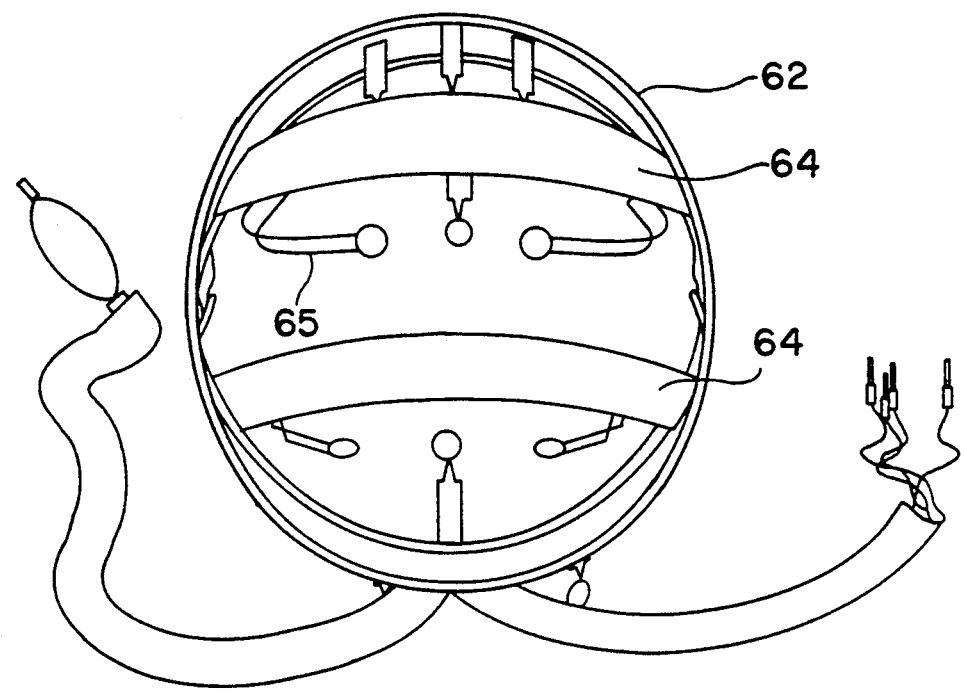
FIGS. 6A and 6B illustrate further modifications of the headset.
Figure 6B:
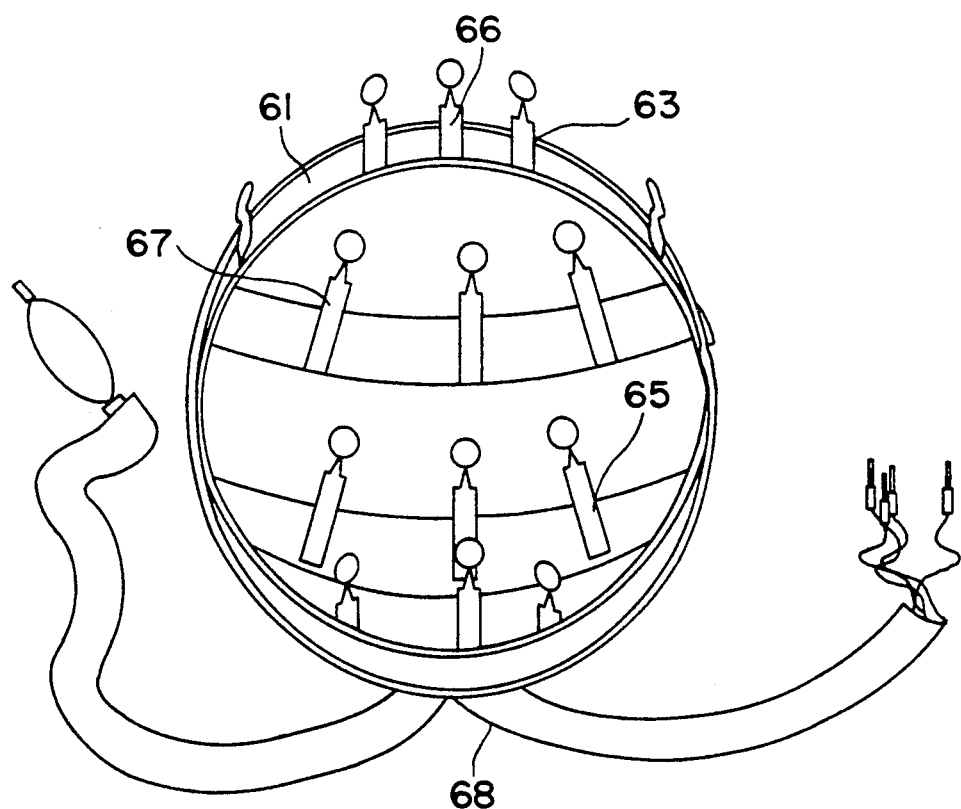

A third modification to the headset is based on the existing air pressure electrode delivery system using a cylinder with movable piston and collapsible bellows. In this embodiment all electrodes are tied to one large pressure cylinder (instead of having small individual cylinders for each electrode) (FIG. 6). This is accomplished by using two ovally formed semirigid plastic strips 61, 62 in order to accommodate all ranges of adult heads (smaller strips are used for the recording of children and small size heads) molded to the circumference of the head. Sandwiched between these two strips is a soft inflatable inner tube which replaces the collapsible bellows of the first and second embodiments. This whole assembly is one piston chamber that conforms to the circumference of the head. The outer strip (62) is now the outer wall of the previous piston. The inner plastic strip (61) has slits (63) cut out that conform to the position of the temporal chain of the previous embodiments (10, 20). The lips of the slits are mobile and replace the piston rod of the piston assembly in the first and second embodiments. With these modifications one piston for the whole headset is realized.

The electrode mounting elements consist of a swing arm attached to the movable lips of the inner strip slits (66, 67). The end of the swing arm is fashioned to accept the recording electrode. Two 1¼" strips are glued transversely to the top of the headset ¼ and ¾ of the distance of the long axis (sagittal) (64). On these transverse strips semirigid swing arms fashioned to accept the recording electrodes (65) are mounted which correspond to the central and parasagittal chain of the previous embodiments (10, 20). In the preferred embodiment conventional Grass E5GH electrodes are used (but the swing arm design can accommodate any other type of electrode). All the electrode wires are harnessed at the back (68). The inflatable tube is attached in the back via a valve to a regular manometer bulb which, when inflated, provides the necessary (and constant) pressure to throw and maintain the electrodes on the scalp. The top electrodes (central and parasagittal), since they are mounted on the semirigid swing arms, extend to the proper scalp location when the headset is placed and adjusted on the head. These electrodes will extend according to the size of the head that the headset has to conform to. The temporal chain electrodes, delivered by the pressurized delivery system when the inner tube is inflated by the manometer bulb, gently pinch the head,, holding the headset in place and because they load perpendicularly to the scalp (as in the previous two embodiments) proper positioning is maintained. By using a syringe filled with gel, electrolyte can be applied to each electrode. In another preferred embodiment an automatic gel delivery system fed via air pressure, through delivery lines, to each electrode, allows the precise delivery of electrolyte to all electrodes.

Numerous modifications and variations are of course possible in light of the principles of the invention disclosed above. All such modifications and variations are intended to be included within the spirit and scope of the invention, as defined in the following claims.

We claim:

1. An electrode assembly in combination with an EEG headset of the type having a headset liner which is placed over the head of patient and which has apertures and mounting elements for mounting respective electrode assemblies therethrough for placing respective electrode tips thereof in contact with the patient's head, said electrode assembly comprising:

an electrode cylinder including a movable piston disposed in an interior part thereof and having a distal end that is to be disposed facing toward the patient's head, at least one mounting element made of a flexible material flexibly mounting the electrode cylinder through a respective aperture in the headset liner, said mounting element having a disk shape and being provided with an inner portion with an annular hole mounting the electrode cylinder therethrough and an outer portion extending beyond the aperture so as to be supported overlapping on the headset liner, an electrode body made of an electrically insulative material having one end portion mounted to the distal end of the piston and an opposite end portion extending away from the distal end of the piston for holding an electrode tip to be placed in contact with the patient's head, and an electrode tip made of a conductive material mounted to said opposite end portion of the electrode body and having a conductive lead encapsulated in an insulative shielding connected thereto for transmitting electrical signals obtained by the electrode tip to an external signal processing unit separately from the electrode cylinder, piston, and other parts of said assembly.

2. An electrode assembly according to claim 1, wherein said at least one mounting element includes a pair of mounting elements spaced apart in parallel for supporting the electrode cylinder from opposite sides of the liner.

3. An electrode assembly according to claim 2, wherein said electrode cylinder has an annular lip on an external surface thereof against which the mounting elements abut.

4. An electrode assembly according to claim 1, wherein said mounting element is a rubber washer with an inner ring which fits onto the electrode cylinder and an outer ring mounted onto the liner which is connected to the inner ring by radial spokes.

5. An electrode assembly according to claim 4, wherein the conductive lead is passed through openings between the radial spokes in the mounting elements and the apertures in the liner for connection to the external signal processing unit.

6. An electrode assembly according to claim 1, wherein said electrode body has a threaded end threaded into a correspondingly threaded receptacle end of the piston.

7. An electrode assembly according to claim 1, wherein said electrode body has a central passage communicating with an inlet connected to a conduit for supplying an electrolyte fluid or gel to the electrode tip.

8. An electrode assembly according to claim 1, wherein said electrode tip has a disk shape with a relatively large surface area and a diameter of about 10 mm.

9. An electrode assembly according to claim 1, wherein said electrode body has a ball joint between its portion for mounting to the piston and its portion for holding the electrode tip.

10. An electrode assembly according to claim 1, wherein the electrode body, piston, and cylinder are all made of non-metallic material.

11. An EEG headset system, comprising:

a headset having a liner provided with apertures mounting respective electrode assemblies therethrough, wherein each electrode assembly includes:

an electrode cylinder including a movable piston disposed in an interior part thereof, at least one mounting element made of a flexible material flexibly mounting the electrode cylinder through a respective aperture in the liner, said mounting element having a disk shape and being provided with an inner portion with an annular hole mounting the electrode cylinder therethrough and an outer portion extending beyond the aperture so as to be supported overlapping on the liner, an electrode body made of an electrically insulative material having one portion mounted to an end of the piston and another portion for holding an electrode tip, and an electrode tip made of a conductive material mounted to an end of the electrode body and having a conductive lead encapsulated in an insulative shielding connected thereto for transmitting electrical signals obtained by the electrode tip to an external signal processing unit separately from the electrode cylinder and other parts of said assembly.

12. An EEG headset system according to claim 11, wherein said electrode tip is removably mounted to the end of said electrode body such that it can be interchanged with another type of electrode tip.

13. An EEG headset system according to claim 11, further including a connector cable, said conductive leads of said electrode assemblies are connected to said connector cable for connection to an external recording device.

* * * * *